United States Patent
Hu et al.

(10) Patent No.: US 8,323,799 B2
(45) Date of Patent: *Dec. 4, 2012

(54) MEDICAL DEVICES HAVING SOFT, FLEXIBLE LUBRICIOUS COATINGS

(75) Inventors: Can B Hu, Irvine, CA (US); Michael D Lowery, Irvine, CA (US); Harish Makker, Mission Viejo, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/282,239

(22) Filed: Oct. 26, 2011

(65) Prior Publication Data

US 2012/0041554 A1 Feb. 16, 2012

Related U.S. Application Data

(62) Division of application No. 11/104,321, filed on Apr. 11, 2005, now Pat. No. 8,053,078.

(51) Int. Cl.
*A61F 2/16* (2006.01)
*A61F 9/00* (2006.01)

(52) U.S. Cl. ............ 428/423.1; 428/420; 428/447; 606/107; 623/6.62

(58) Field of Classification Search .......... 525/124, 525/130, 332.8
See application file for complete search history.

(56) References Cited

U.S. PATENT DOCUMENTS

| | | |
|---|---|---|
| 4,373,009 A | 2/1983 | Winn |
| 4,657,820 A | 4/1987 | Halpern et al. |
| 4,681,102 A | 7/1987 | Bartell |
| 4,792,414 A | 12/1988 | Su et al. |
| 4,801,475 A | 1/1989 | Halpern et al. |
| 4,876,126 A | 10/1989 | Takemura et al. |
| 4,919,130 A | 4/1990 | Stoy et al. |
| 5,023,114 A | 6/1991 | Halpern et al. |
| 5,026,607 A | 6/1991 | Kiezulas |
| 5,037,677 A | 8/1991 | Halpern et al. |
| 5,229,211 A | 7/1993 | Murayama et al. |
| 5,272,012 A | 12/1993 | Opolski |
| 5,308,641 A | 5/1994 | Cahalan et al. |
| 5,415,938 A | 5/1995 | Cahalan et al. |
| 5,499,987 A | 3/1996 | Feingold |
| 5,582,613 A | 12/1996 | Brady et al. |
| 5,607,475 A | 3/1997 | Cahalan et al. |
| 5,647,985 A | 7/1997 | Ung-Chhun et al. |
| 5,702,754 A | 12/1997 | Zhong |
| 5,702,818 A | 12/1997 | Cahalan et al. |
| 5,716,364 A | 2/1998 | Makker et al. |
| 5,782,908 A | 7/1998 | Cahalan et al. |
| 5,803,925 A | 9/1998 | Yang et al. |
| 5,804,318 A | 9/1998 | Pinchuk et al. |
| 5,811,151 A | 9/1998 | Hendriks et al. |
| 5,866,113 A | 2/1999 | Hendriks et al. |
| 5,941,886 A | 8/1999 | Feingold |
| 5,942,277 A | 8/1999 | Makker et al. |
| 6,083,230 A | 7/2000 | Makker et al. |
| 6,146,771 A | 11/2000 | Wirt et al. |
| 6,187,369 B1 | 2/2001 | Beavers |
| 6,238,799 B1 | 5/2001 | Opolski |
| 6,241,766 B1 | 6/2001 | Liao et al. |
| 6,245,106 B1 | 6/2001 | Makker et al. |
| 6,248,111 B1 | 6/2001 | Glick et al. |
| 6,270,902 B1 | 8/2001 | Tedeschi et al. |
| 6,283,975 B1 | 9/2001 | Glick et al. |
| 6,306,454 B1 | 10/2001 | Ung-Chhun et al. |
| 6,309,660 B1 | 10/2001 | Hsu et al. |
| 6,340,465 B1 | 1/2002 | Hsu et al. |
| 6,361,561 B1 | 3/2002 | Huo et al. |
| 6,398,788 B1 | 6/2002 | Makker et al. |
| 6,451,871 B1 | 9/2002 | Winterton et al. |
| 6,679,891 B2 | 1/2004 | Makker et al. |
| 6,866,936 B2 | 3/2005 | Opolski |
| 8,053,078 B2 | 11/2011 | Hu et al. |
| 2002/0133167 A1 | 9/2002 | Harish et al. |
| 2003/0014107 A1 | 1/2003 | Reynard |
| 2003/0065051 A1 | 4/2003 | Winterton et al. |
| 2003/0195522 A1 | 10/2003 | McNicholas et al. |
| 2003/0216745 A1 | 11/2003 | Brady et al. |
| 2004/0068225 A1 | 4/2004 | Ung-Chhun et al. |
| 2005/0147735 A1 | 7/2005 | Lowery et al. |

FOREIGN PATENT DOCUMENTS

| | | |
|---|---|---|
| JP | 4095024 A | 3/1992 |
| JP | 11514278 T | 12/1999 |
| JP | 2000507997 T | 6/2000 |
| JP | 2000514333 T | 10/2000 |
| WO | WO9623834 A1 | 8/1996 |

OTHER PUBLICATIONS international Preliminary Report on Patentability and Written Opinion for Application No. PCT/US2006/013392, mailed on Oct. 16, 2007, 6 pages.
International Search Report for Application No. PCT/US2006/13392, mailed on Aug. 9, 2006, 2 pages.

*Primary Examiner* — Walter Webb
(74) *Attorney, Agent, or Firm* — Abbott Medical Optics Inc.

(57) ABSTRACT

Soft, flexible highly lubricious coatings for polymeric IOL insertion cartridges that allow IOLs to be easily inserted through small bore cartridges suitable for use with small (less than 3 mm) incisions are provided. These lubricious coatings allow IOLs to be inserted into the eye of a patient without the risk of lens damage or transfer of lubricants to the lens surface during implantation. Specifically, polymeric coatings comprising a matrix polymer having an equivalent weight greater than 5000 g/eq are used to form interpenetrating networks (IPN) on the surface of hydrophobic structural polymers. The IPNs thus formed entrap highly lubricious hydrophilic compounds within the IPN using multi-functional cross linkers.

3 Claims, No Drawings

MEDICAL DEVICES HAVING SOFT, FLEXIBLE LUBRICIOUS COATINGS

This application is a divisional application and claims priority to U.S. application Ser. No. 11/104,321, entitled Medical Devices Having Soft, Flexible Lubricious Coatings, filed on Apr. 11, 2005, the entire contents of which is hereby incorporated by reference in its entirety for all purposes as if fully set forth herein.

FIELD OF THE INVENTION

The present invention relates to medical devices having soft, flexible, lubricious coatings. Specifically, the present invention relates to pliable medical devices having soft, flexible, lubricious coatings. More specifically, the present invention relates to intraocular lens insertion cartridges provided with stable, soft, flexible, lubricious coatings that do not transfer to the lens surface or delaminate or fragment during use.

BACKGROUND OF THE INVENTION

Intraocular lenses (IOL) are generally implanted in the eye as a replacement for the natural crystalline lens following cataract surgery or to alter the optical properties of (provide vision correction to) an eye in which the natural lens remains. Intraocular lenses often include an optic, and preferably at least one flexible fixation member or haptic which extends from the optic and becomes affixed in the eye to secure the lens in position. The optic normally includes an optically clear lens. Implantation of such IOLs into the eye involves making an incision in the eye. It is advantageous to have an incision size as small as possible to reduce trauma and speed healing.

IOLs are known which are foldable (deformable) so that the IOL can be inserted through a smaller incision into the eye. A substantial number of instruments have been proposed to aid in inserting such a foldable lens in the eye.

However, whether using a distal loading or proximal loading system, one factor which limits the size of the inserter tube (cartridge) involves the inserter tube itself. For example, the material from which the inserter tube is made (i.e., polypropylene and like polymeric materials) may not be compatible with or otherwise susceptible to causing optics (e.g., made from silicone polymeric materials) to pass through relatively small hollow spaces. For example, the injector cartridges may be made of materials, in particular polymeric materials, which have insufficient lubricity to facilitate the passage of a folded IOL through the cartridge.

As a result of this lack of lubricity, the hollow space of the injector cartridge must be made relatively larger to accommodate the folded intraocular lens. This is detrimental because, as noted above, it is advantageous to have the smallest possible incision for insertion of the IOL. In addition, if one were to use a small diameter cartridge to pass the IOL, excessive force might be needed to pass the IOL through the small hollow space thereby increasing the risks of damaging the IOL and, in extreme cases, even damaging the eye into which the IOL is placed.

One approach that may be considered is to use a lubricity agent, for example, such as conventional visco-elastic agents, in the hollow space of the cartridge to facilitate passing the COL through the insertion apparatus. However, such lubricity agents occupy valuable space, thereby at least partially defeating the purpose of using such agents. Also, such lubricity agents often end up in the eye, thereby creating the risk of causing trauma and/or irritation and/or damage to the eye.

Several different techniques are utilized to apply coatings to the surface of an IOL insertion cartridge. U.S. Pat. No. 5,716,364 issued to Makker et al. on Feb. 10, 1998 (hereinafter the Makker patent, the entire contents of which are incorporated herein by reference) discloses and claims an IOL insertion cartridge fabricated from a hydrophobic structural polymer such as polypropylene. During the manufacturing steps a lubricity enhancing composition such as a fatty acid ester is incorporated into the hydrophobic structural polymer resin. The fabricated cartridge is then subjected to elevated temperatures for a time period that is effective to cause the lubricity enhancing component (for example glycerol monosterate [GMS]) to migrate toward the cartridge's interior surface. A common name for this phenomenon is "blooming." However, while the bloomed GMS provides an effective lubricious coating, the fatty acid ester continues to deposit on the cartridge surface over time. Consequently, after prolonged storage sufficient GMS can be present on the interior surface of the cartridge such that the IOL becomes streaked with lubricant during the insertion process. Thus, the cartridges' shelf life is less than optimal.

Another method for providing lubricous coatings for IOL insertion cartridges is described in U.S. Pat. Nos. 6,238,799 and 6,866,936, both issued to Opolski on May 29, 2001 and Mar. 15, 2005, respectively (hereinafter the Opolski patents, the entire contents of which are incorporated by reference). The Opolski patents disclose forming interpenetrating networks (IPN) on the surface of hydrophobic structural polymers using a supporting polymer selected from the group consisting of polyacrylates, polymethacrylates, polyurethanes, polyethylene and polypropylene copolymers, polyvinyl chlorides, epoxides, polyamides, polyesters and alkyl copolymers. The supporting polymer is first blended with a hydrophilic polymer selected from the group consisting of poly(N-vinyl lactams), poly(vinylpyrrolidone), poly(ethylene oxide) poly(propylene oxide) polyacrylamides, cellulosics, methyl cellulose, polyacrylic acids, polyvinyl alcohols, and polyvinyl ethers and at least one cross-linking agent and then applied to the surface of the IOL insertion cartridge. The IPNs formed according to the teaching of Opolski patents are relatively rigid and inflexible due to the supporting polymers' high equivalent weights of the functional moieties. For example, Opolski provides equivalent weights in the range of about 115 to about 8700. In one embodiment Opolski provides a supporting polymer of polyacrylate and the equivalent weight of the functional moiety is in the range of about 200 to about 1000; a polyurethane supporting polymer having equivalent weights of the functional moiety in the range of about 1000 to about 8700 and a polyamine epoxide supporting polymer having equivalent weights of the functional moiety is in the range of about 100 to about 2000. Consequently, the lubricious coatings disclosed and claimed in the Opolski patents are relatively rigid and can potentially damage the IOL during the insertion process.

Therefore, it would be advantageous to provide IOL insertion cartridges with flexible, soft lubricious coatings having long shelf-lives that do not damage the IOL or transfer substantial amounts of lubricant to the IOL surfaces during insertion.

SUMMARY OF THE INVENTION

The present invention addresses the problem associated with the prior art as described above by providing intraocular lens (IOL) insertion cartridges with soft, flexible lubricious coatings having long shelf-lives that do not damage the IOL or transfer substantial amounts of lubricant or debris to the IOL surfaces during insertion. These and other objects of the present invention are achieved in part by providing IOL insertion cartridge coatings comprising polymeric interpenetrating networks comprising a polymer matrix material having a relatively high equivalent weight of functional moieties blended with hydrophilic lubricious molecules and at least one cross-linking agent. In other embodiments, additional performance enhancing coating additives including but not limited to, ultraviolet light absorbents, preservatives, antimicrobials, dyes, initiators, defoamers, emulsifiers, wetting enhancers and the like are added the coating compositions of the present invention.

In one embodiment of the present invention the IOL insertion cartridge comprise a structural polymer including, but not limited to, polypropylene that has been provided with a soft lubricious coating. The coatings made in accordance with the teachings of the present invention comprise an aqueous-based solvent-compatible polymer matrix material comprising a plurality of cross-linkable functional moieties, a hydrophilic lubricant and a multi-functional cross-linker. The hydrophilic lubricant interacts with the polymer matrix material via intermolecular forces such as dipole-dipole, hydrogen bonding, and Van der Waals forces (i.e., non-covalent bonds). The polymer matrix material is then cross-linked at the functional moieties so as to form a three-dimensional network (an interpenetrating network, or IPN which substantially eliminates disassociation of the hydrophilic polymer.

In one embodiment of the present invention the soft, lubricous coating comprises a polymer matrix material comprising a water-based urethane solution having an equivalent weight of the functional moieties above 5,000 g/eq, and preferably above 10,000 g/eq; a hydrophilic lubricant selected from the group consisting of polyvinylpyrrolidine (PVP), polyethylene oxide (PEO) and hyaluronic acid and a polyfunctional cross-linker including, but not limited to, aziridines, polyfunctional carbodiimides, polyfunctional epoxides, unsaturated carbon and heteroatom bonds, ionic agents, divalent cations and melamine/urea condensates.

The present invention also provides methods for making the IOL insertion cartridge coatings. For example, in one embodiment of the present invention a mixture is prepared comprising a water soluble multi-functional urethane having a functional moiety equivalent weight of greater than 5000 g/eq (matrix polymer) is mixed with PVP (hydrophilic lubricant), aziridines (cross-linker) and suitable additives (the coating solution). The coating solution thus prepared is then applied to the surfaces of a polypropylene IOL inserter cartridge using a method selected from the group consisting of dipping, rolling, brushing and spraying. Any excess coating mixture is removed and the coated IOL inserter cartridge is dried over night at elevated temperatures (relative to ambient). In another embodiment of the present invention hyaluronic acid is substituted for PVP in the embodiment immediately above.

In other embodiments of the present invention the IOL inserter cartridge surface is pretreated prior to coating. The pretreatment may be selected from the group consisting of chemical etching, corona and plasma treatment (etching), priming with other chemicals, coatings and adhesives and mechanical abrasion. In a preferred embodiment plasma treatment is done using a nitrous oxide/helium mixture rather than an atmosphere of pure oxygen.

DETAILED DESCRIPTION OF THE INVENTION

A. Definition Of Terms

Equivalent Weight: As used herein "equivalent weight" refers to the amount of functional moiety in the matrix polymer which is defined as the weight of matrix polymer per one equivalent of functional moiety in the polymer; thus, the greater the number, the lower the level of functional moiety in the matrix polymer. Equivalent weight as used herein is expressed in grams per equivalent (g/eq). Occasionally, resin manufacturers may refer to "acid number" rather than equivalent weight. Acid number is related to equivalent weight according to the flowing equation:

$$\text{Equivalent weight} = 56{,}100/\text{acid number}$$

Functional Moiety: As used herein "functional moiety" is synonymous with "functional group" and refers to the reactive site on the matrix polymer involved in, or susceptible to, cross-linking. Non-limiting examples commonly found in matrix polymers include, amino, hydroxyl, amido, carboxylic acid and derivatives thereof, sulfhydryl (SH), unsaturated carbon and heteroatom bonds, just to name a few. In one embodiment of the present invention urethane is the matrix polymer and carbonyl-containing functional groups such as oxo and amine nitrogens are present.

Hydrophilic lubricant: As used herein "hydrophilic lubricant" refers to the lubricious polymer entrapped in the IPN formed by cross-linking the matrix polymer. In one embodiment of the present invention the hydrophilic lubricant is selected from the group consisting of polyvinylpyrrolidine (PVP), polyethylene oxide (PEO) and hyaluronic acid.

Matrix Polymer: As used herein "matrix polymer" refers to the water (aqueous phase compatible) soluble polymer which makes up the cross-linkable component of the inter-penetrating network (IPN) and generally comprises the "functional moieties." In one embodiment of the present invention the matrix polymer is urethane.

Structural polymer: As used herein "structural polymer" refers to the polymeric material used to make the IOL inserter cartridge itself (also referred to alternatively as the hydrophobic structural polymer substrate). For example, in the present embodiment of the present invention, the IOL inserter cartridge comprises polypropylene and is made by Advanced Medical Optics, Santa Ana, Calif. for use with its Emerald Unfolder line of IOL inserters.

B. Description Of Preferred Embodiments

It is desirable to minimize patient discomfort and recovery time for patients undergoing surgical replacement of one or more crystalline lenses of the eye. Recent advancements in replacement intraocular lens (IOL) design and construction have resulted in IOLs comprised of resilient, durable, highly polymers that can be inserted through extremely small (less than 3 mm) incisions. For example, see U.S. Pat. Nos. 6,241, 766; 6,245,106 and 6,361,561, the entire contents of which are herein incorporated by reference.

However, deformable IOLs suitable for injection through small incisions are generally made from hydrophobic polymers such as acrylates, polysiloxanes and silicones. Consequently, these lenses can bind to the IOL inserter cartridge during delivery due to the high coefficient of friction between the cartridge's structural polymer and the IOL material. As a result the operator must apply significant pressure to the proximal end (plunger or screw) of the insertion device in order to advance the IOL (see U.S. Pat. No. 5,582,613 as a representative example of an insertion device used in conjunction with the present invention; the entire contents of which are incorporated herein by reference). Occasionally resistance is so severe that the IOL may be torn, the IOL inserter cartridge may burst or lens delivery may fail completely.

Furthermore, efforts to provide IOL inserter cartridges with lubricous coatings having reduced coefficients of friction have only been partially successful. One approach taken by skilled practitioners has been to develop structural polymers such as polypropylene having lubricious fatty acids such as glycerol monosterate incorporated into the structural polymer blend during IOL cartridge molding (see U.S. Pat. No. 5,716,364 to Makker at al.). After the cartridge has been formed, the inserter cartridge is heated to a temperature above ambient to promote "blooming" of the GMS on the surfaces of the polymer cartridge. While this approach has resulted in IOL inserter cartridges having superior lubricious properties and thus eliminated the aforementioned problems with IOL binding during deployment, the GMS continues to "bloom" and accumulate on the IOL inserter cartridge surfaces during storage. After prolonged storage GMS accumulation becomes so great that an IOL inserted using the stored cartridge becomes streaked with GMS. This quality is not optimal, although not harmful to the patient. Thus, IOL insertion cartridges made having "blooming" GMS lubricants incorporated into the structural polymer typically have undesirably short-shelf-lives.

Another method for providing lubricous coatings for IOL insertion cartridges is described in U.S. Pat. Nos. 6,238,799 and 6,866,936, both issued to Opolski (hereinafter the Opolski patents). The Opolski patents disclose forming interpenetrating networks (IPN) on the surface of hydrophobic structural polymers using a supporting polymer selected from the group consisting of polyacrylates, polymethacrylates, polyurethanes, polyethylene and polypropylene copolymers, polyvinyl chlorides, epoxides, polyamides, polyesters and alkyl copolymers. The supporting polymer is first blended with a hydrophilic polymer selected from the group consisting of poly(N-vinyl lactams), poly(vinylpyrrolidone), poly (ethylene oxide) polypropylene oxide) polyacrylamides, cellulosics, methyl cellulose, polyacrylic acids, polyvinyl alcohols, and polyvinyl ethers and at least one cross-linking agent and then applied to the surface of the IOL insertion cartridge. The IPNs formed according to the teaching of Opolski patents are relatively rigid and inflexible due to the supporting polymers' high equivalent weights of the functional moieties. For example, Opolski provides equivalent weights in the range of about 115 to about 8700. In one embodiment Opoiski provides a supporting polymer of polyacrylate and the equivalent weight of the functional moiety is in the range of about 200 to about 1000; a polyurethane supporting polymer having equivalent weights of the functional moiety in the range of about 1700 to about 2800 and a polyamine epoxide supporting polymer having equivalent weights of the functional moiety is in the range of about 100 to about 2000. Consequently, the lubricious coatings disclosed and claimed in the Opolski patents are relatively rigid and can potentially damage the IOL during the insertion process.

Moreover, the present inventors have surprisingly discovered that mixing coating constituents thoroughly at high speeds is useful for making homogeneous coating solutions in accordance with the teachings of the present invention. A homogeneous coating solution is needed to assure that stable, non-delaminating IPNs form on the cartridge surface. Opolski is silent regarding mixing parameters necessary to obtain homogenous coating compositions; however, the present inventors have discovered that satisfactory coatings made in accordance with the teachings of the present invention are achieved when a mechanical stirring apparatus generating a minimum agitation speed of approximately 300 rpm is used. Suitable examples of stirring devices include, without limitation, Stirrer Motor, Model RW16 Basic, IKA Works (VWR International). In other embodiments of the present invention mechanical stirring devices including magnetic stir plate and stir bar apparatuses may be suitable.

The ideal IOL insertion apparatus suitable for delivery of a foldable IOL through a small-incision (less than 3 mm, preferably less than 2 mm) must employ an inserter cartridge having a highly lubricious interior IOL passageway. The lubrication system used for IOL insertion apparatuses must minimize the force required for IOL placement such that the inserter, the lens and patient's eye are not damaged during the procedure (the former two parameters typically leading to the third). Typically, this means that the lubricant system must reduce the torque required to deploy the IOL to below 1000 g/cm; ideally less than 500 g/cm. Moreover, the IOL passage way must not release significant quantities of lubricants onto the IOL surface (streak the lens) or leave visible debris on the implanted lens. Significant as used herein means that the lubrication system must not impart a film or leave visible debris or aberrations to the IOL surface when examined at about 15× magnification during a slit-lamp evaluation.

Towards that end, the present inventors have surprisingly discovered that by increasing the equivalent weight of the matrix polymer, a highly lubricious coating can be achieved that is more durable and softer than prior art coatings and thus does not streak or otherwise damage the IOL during the insertion process. Moreover, by using matrix polymers having substantially higher equivalent weights than disclosed in prior art coating compositions, the present inventors believe that considerably more hydrophilic lubricous materials can be integrated into the IPN of the present invention. The matrix polymers of the present invention comprise acrylic urethane and urethane/acrylic solutions wherein the cross-linking density of the resulting IPN is controlled by selecting polymer precursors having the appropriate equivalent weight. In one embodiment of the present invention the IOL inserter cartridge coating comprises a water soluble (aqueous-based solvent compatible) urethane matrix polymer having an equivalent weight greater than 5000 g/eq. In another embodiment of the present invention the equivalent weight of the urethane matrix polymer is between approximately 5000 g/eq and 15,000 g/eq. In one embodiment of the present invention the equivalent weight of the urethane matrix polymer is between approximately 5,000 g/eq and 12,000 q/eq. In another embodiment of the present invention the equivalent weight of the urethane matrix polymer is between approximately 10,000 g/eq and 12,000 q/eq.

The urethane martrix polymer of the present invention is mixed with a hydrophilic lubricious compound including, but not limited to, polyvinylpyrrolidine (PVP), polyethylene oxide (PEO) and hyaluronic acid and a multi-functional cross-linker including, but not limited to, aziridines, polyfunctional carbodilmides, polyfunctional epoxides, unsaturated carbon and heteroatom bonds, ionic agents, divalent cations (Mg++, Mn++, Zn ++ and/or Ca++) and melamine/urea condensates.

The coating mixture thus formed (urethane matrix polymer, hydrophilic lubricious compound, cross-linker and optionally other performance enhancing compositions) is applied to the surfaces of an IOL inserter cartridge comprised of a hydrophobic structural polymer substrate including, but not limited to, polypropylene. In one embodiment of the present invention the hydrophobic structural polymer substrate is pretreated using a method selected from the group consisting of chemical etching, corona and plasma treatment (etching), priming with other chemicals, coatings and adhesives and mechanical abrasion.

In one embodiment plasma etching is done using a nitrous oxide/helium mixture rather than an atmosphere of pure oxygen. The resulting plasma etching performed in a nitrous oxide/helium atmosphere generates highly reactive carboxyl groups on the polypropylene surface which chemically react with the urethane's carbonyl-functionalized residues. Consequently the matrix polymer is covalently bound to the structural polymer's surface providing for a securely anchored IPN. Methods for plasma treating polymers are widely known in the art and will not be detailed herein. Persons having ordinary skill in the art will be able optimize plasma etching processes useful for practicing the present invention without undue experimentation. The surprising factor is the present inventors' discovery that plasma etching in a non-oxygen environment, e.g. a nitrous oxide/helium atmosphere, provides for superior covalent attachment of the urethane matrix polymer to the polypropylene structural polymer.

The coating compositions of the present invention may include one or more performance enhancing composition including, but not limited to, ultraviolet (UV) light absorbers, anti-foam reagents, de-foaming reagents, wetting solutions, detergents, emulsifiers, preservatives, anti-thrombogenic compounds, anti-coagulants, anti-inflammatories, cytostatic compounds, cytotoxic compounds, antibiotics, analgesics, and the like.

C. EXAMPLES

Example 1

Polyvinylpyrrolidine (PVP) Coating

In a glass flask 30.15 g urethane R9330,(equivalent weight 11,688 g/eq) (NeoResins, Wilmington, Mass.), 1.82 g PVP (ISP, Wayne, N.J.), 0.78 g of poly functionalized aziridines (NeoResins, Wilmington, Mass.), 0.05 g wetting enhancer (BYK-348) (BYK-Chemie USA, Walingford, Conn.), 0.09 g defoamer (BYK-24) (BYK-Chemie USA, Walingford, Conn.) and 92.07 g deionized water were mixed thoroughly using Stirrer Motor, Model RW16 Basic, IKA Works, VWR International). Speeds between 300 rpm and 1200 rpm were used to form a PVP coating solution. The PVP coating solution was applied to the interior surfaces (IOL passage way) of plasma etched polypropylene IOL inserter cartridges. (Plasma etching was performed in a helium/nitrous oxide atmosphere.) The cartridges were treated with the PVP coating solution for 3 minutes at room temperature. After soaking the cartridges for 3 minutes excess coating solution was removed and the cartridges were dried overnight at 60° C.

Example 2

Hyaluronic Acid (HA) Coating

In a glass flask 30.15 g urethane R9330, (equivalent weight 11,688 g/eq; acid number 4.6) (NeoResins, Wilmington, Mass.), 1.21 g HA (Fluka Chemicals purchased through Sigma Chemicals, St. Louis, Mo.), 0.78 g of poly functionalized aziridines (NeoResins, Wilmington, Mass.), and 92.07 g deionized water were mixed vigorously (equal to or greater than 300 rpm using Stirrer Motor, Model RW16 Basic, IKA Works, VWR International) to form a HA coating solution. The HA coating solution was applied to the interior surfaces (IOL passage way) of plasma etched polypropylene IOL inserter cartridges. The cartridges were treated with the HA coating solution for 3 minutes at room temperature. After soaking the cartridges for 3 minutes excess coating solution was removed and the cartridges were dried overnight at 60° C.

Post coating testing was conducted to determine the amount of force required to deploy an IOL through the coated IOL inserter cartridge. Coated and uncoated Advanced Medical Optics polypropylene cartridges were tested and the results were compared. Uncoated Emerald brand inserter cartridges were used to deploy 20 and 30 diopter IOLs. Testing was conducted at room temperature using a Data Instrument (Acton, Mass.) torque gage. The average torque requires to deliver the 20 diopter IOLs was 739 g/cm and 886 g/cm for the 30 dioptor lenses (mean lens thickness increases slightly with diopter increase) through the uncoated cartridges. However, Emerald brand cartridges coated as described in Examples 1 and 2 resulted in an average torque of 260 g/cm for 28 diopter lenses. Thus the coating process resulted in an overall improvement in lubricity of between approximately 280 and 340 percent.

A second series of tests were conducted using a Chatillon Digital Force gauge to compare coated and uncoated Connect IOL inserter cartridges (manufactured by Canon-Starr). Uncoated Connect IOL inserter cartridges jammed and resulted in destruction of the IOL. However, after coating the Connect cartridge according to embodiments of the present invention the IOLs were delivered easily and without obstruction or excessive force.

Additionally, the glass transition temperature (Tg) of the coating polymer made in accordance with the teachings of the present invention confirmed a Tg equal to or less than −50° C. Glass transition temperatures at or near this point are consistent with soft pliable polymers.

D. Conclusion

Natural crystalline lens replacement procedures are becoming increasingly more popular with patients as alternatives to cataracts and other natural crystalline lens-related diseases. Moreover, recent advances in natural crystalline lens replacement surgery have made IOLs an alternative to other surgical procedures to correct refractive errors. Therefore, methods and materials related to providing IOL insertion procedures that reduce patient discomfort and recovery times are urgently needed.

The present invention provides soft, flexible highly lubricious coatings for polymeric IOL insertion cartridges that allow IOLs to be easily inserted through small bore cartridges suitable for use with small (less than 3 mm) incisions. The lubricious coatings made in accordance with the teachings of the present invention allow IOLs to be inserted into the eye of a patient without the risk of lens damage or transfer of lubricants and debris to the lens surface during implantation. Specifically, the present invention provides novel polymeric coatings comprising a matrix polymer having an equivalent weight greater than 5000 g/eq used to form interpenetrating networks (IPN) on the surface of hydrophobic structural polymers. The IPNs thus formed entrap highly lubricious hydrophilic compounds within the IPN using multi-functional cross linkers.

Unless otherwise indicated, all numbers expressing quantities of ingredients, properties such as molecular weight, reaction conditions, and so forth used in the specification and claims are to be understood as being modified in all instances by the term "approximately." Accordingly, unless indicated to the contrary, the numerical parameters set forth in this specification and attached claims are approximations that may vary depending upon the desired properties sought by the present invention. At the very least, and not as an attempt to limit the application of the Doctrine of Equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illustrate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An IOL inserter cartridge having a soft coating consisting essentially of:
    a urethane matrix polymer having an equivalent weight between 10,000g/eq. and 15,000 g/eq;
    a hydrophilic lubricious lubricant consisting essentially of hyaluronic acid; and
    a multi-functional cross-linker consisting essentially of poly-functional aziridine.

2. The IOL inserter cartridge according to claim 1 wherein said urethane matrix polymer has an equivalent weight of approximately 11,688g/eq.

3. The IOL inserter cartridge according to claim 1 or 2 further comprising at least one performance enhancing composition selected from the group consisting of ultraviolet light absorbers, anti-foam reagents, de-foaming reagents, wetting solutions, detergents, emulsifiers, preservatives, anti-thrombogenic compounds, anti-coagulants, anti-inflammatories, cytostatic compounds, cytotoxic compounds, antibiotics, and analgesics.

* * * * *